United States Patent
Reynolds

(10) Patent No.: US 6,302,303 B1
(45) Date of Patent: Oct. 16, 2001

(54) DISCRETE LIQUID TRANSPORT AND DISCHARGE APPARATUS AND METHOD

(76) Inventor: Robert Reynolds, 2934 Mann St., Las Vegas, NV (US) 89146

( * ) Notice: Subject to any disclaimer, the term of this patent is extended or adjusted under 35 U.S.C. 154(b) by 0 days.

(21) Appl. No.: 09/792,158

(22) Filed: Feb. 26, 2001

(51) Int. Cl.[7] .................................................. B67D 5/64
(52) U.S. Cl. ..................... 222/175; 222/146.2; 222/215
(58) Field of Search ................................. 222/175, 146.2, 222/527, 529, 215; 604/331

(56) References Cited

U.S. PATENT DOCUMENTS 5,735,835 * 4/1998 Holland ................................ 604/331
6,032,831 * 3/2000 Gardner et al. ...................... 222/175

* cited by examiner

Primary Examiner—Philippe Derakshani
(74) Attorney, Agent, or Firm—Weiss & Moy, P.C.; Harry M. Weiss; Jeffrey Weiss

(57) ABSTRACT

An apparatus and method for transporting a liquid on the body of a person and discharging the liquid. The apparatus consists of a liquid container that is dimensioned so that a top portion thereof may be inserted between the buttocks of a user. The liquid container is connected to a hose, which is of sufficient length to pass between a user's legs. The hose is capped, so as to prevent accidental discharge of the contained liquid. In the preferred embodiment, the temperature of the contained liquid may be maintained by lining the base of the liquid container with an insulation material and, where necessary, positioning a heat packet within an opening in the insulation material.

17 Claims, 1 Drawing Sheet

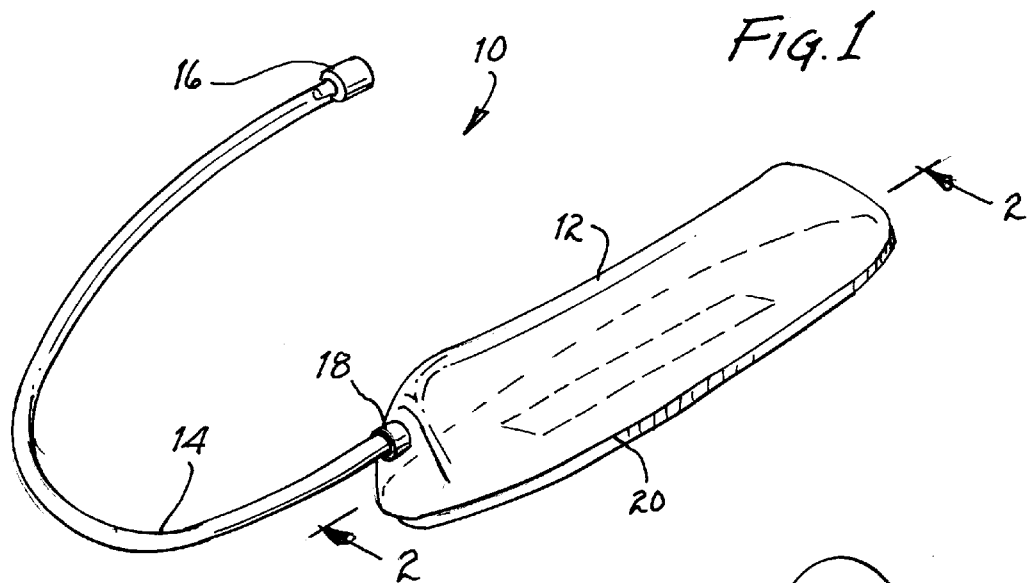
FIG. 1
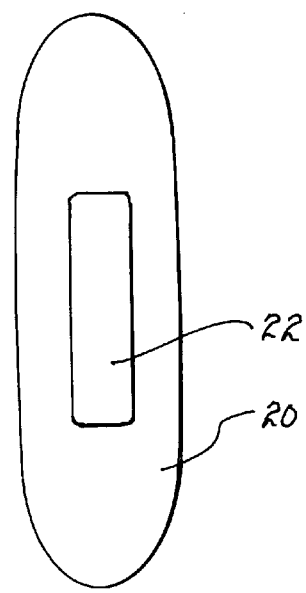
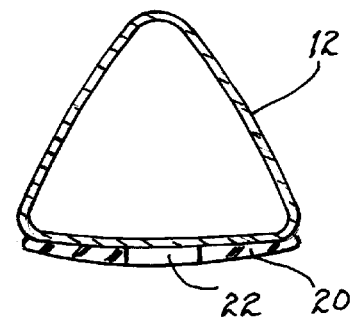
FIG. 3
FIG. 4
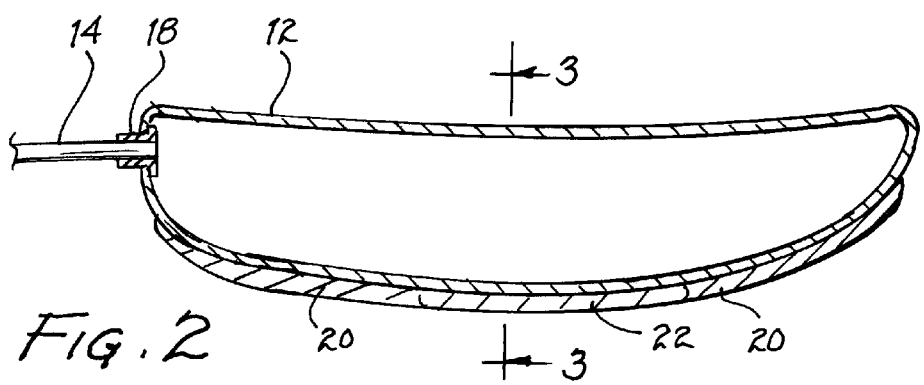
FIG. 2

DISCRETE LIQUID TRANSPORT AND DISCHARGE APPARATUS AND METHOD

FIELD OF THE INVENTION

This invention relates generally to apparatuses for the transport of liquids in a discrete manner and methods therefor and, more specifically, to an apparatus and method for discretely transporting on a person's body a liquid, and discharging that liquid in a discrete manner.

BACKGROUND OF THE INVENTION

For a variety of reasons, persons may wish to carry a liquid in a discrete manner on their person. For example, where lawful to do so, a person required to provide a urine sample may wish to provide a sample of known content, and may wish to carry and discharge that sample in a manner not readily apparent to those observing the provision of the sample. URINE LUCK© is the federal trademark for a clean urine sample that may be purchased for use in a urine test. However, this product may not be readily transported to the site of such a test, and cannot be discretely provided where a sample must be given in the presence of a third party.

In addition, a man wishing to play a practical joke may wish to carry a non-yellow liquid on his person, and then to discharge that liquid as though it were a waste product. Still further, for military, espionage, or law enforcement purposes, it may be necessary to transport and discharge a liquid in a manner not readily discernible to outsiders.

It is the purpose of the present invention to provide an apparatus and method permitting such discrete transportation and discharge of liquids, such as urine.

SUMMARY OF THE INVENTION

An object of the present invention is to provide an apparatus and method for discretely transporting a liquid on the body of a person.

A further object of the present invention is to provide an apparatus and method for discretely transporting a liquid on the body of a person and discharging that liquid in a discrete manner.

BRIEF DESCRIPTION OF THE PREFERRED EMBODIMENTS

In accordance with one embodiment of the present invention, an apparatus for transporting a liquid on the body of a person and discharging the liquid is disclosed. The apparatus comprises, in combination: a container adapted to contain a liquid; wherein the container is dimensioned so that an upper portion thereof can be inserted between a person's buttocks; a hose coupled at a first end thereof to the container; and one of a cap, valve, and plug inserted into a second end of the hose; wherein the hose is of sufficient length to pass between the person's legs.

In accordance with another embodiment of the present invention, a method for transporting a liquid on the body of a person and discharging the liquid is disclosed. The method comprises: providing a container adapted to contain a liquid; placing the liquid in the container; wherein the container is dimensioned so that an upper portion thereof can be inserted between a person's buttocks; providing a hose coupled at a first end thereof to the container; providing one of a cap, valve, and plug inserted into a second end of the hose; wherein the hose is of sufficient length to pass between the person's legs; inserting said upper portion of said container between the person's buttocks; positioning the hose between the person's legs.

The foregoing and other objects, features, and advantages of the invention will be apparent from the following, more particular description of the preferred embodiments of the invention, as illustrated in the accompanying drawings.

BRIEF DESCRIPTION OF THE DRAWINGS

FIG. 1 is a perspective view of the liquid transport and discharge apparatus of the present invention.

FIG. 2 is a side, cross-sectional view of the container portion of the apparatus of FIG. 1, taken along line 2—2 of FIG. 1.

FIG. 3 is an end, cross-sectional view of the container portion of the apparatus of FIG. 1, taken along line 3—3 of FIG. 2.

FIG. 4 is a bottom view of the container portion of the apparatus of FIG. 1.

DETAILED DESCRIPTION OF THE PREFERRED EMBODIMENTS

Referring first to FIG. 1, the liquid transport and discharge apparatus 10 (hereinafter "apparatus 10") of the present invention is shown. The basic component portions of the apparatus 10 are the liquid container 12, the hose 14, and the cap 16 inserted into the open end of the hose 14. These will now be discussed in more detail.

Beginning with the liquid container 12, it should be dimensioned so that at least an upper portion thereof can be inserted between a person's buttocks. Preferably, as shown in FIGS. 1 and 3, the liquid container 12 will have a wedge shape, with the thin edge dimensioned to be inserted between a person's buttocks—so as to maintain the liquid container 12 in a stable position during wearing and movement. When positioned properly, the base of the liquid container 12 can rest upon the person's undergarment.

The liquid container 12 should, of course, be of a watertight material. Preferably, the liquid container 12 is also flexible, so as to provide increased comfort to the user. Suitable materials include vinyl, plastic and rubber. As shown in FIGS. 1 and 2, the liquid container 12 is coupled to the hose 14 with a hose connector 18. Like the liquid container 12, it is preferred that the hose 14 be flexible, and suitable materials would include vinyl, plastic and rubber.

At its discharge end, the hose 14 is closed with a cap 16. The term cap as used herein shall be interpreted to include any device capable of regulating the passage of liquid out of the discharge end of the hose 14, including caps, valves (including turn valves), plugs and similar devices.

The hose 14 should be of sufficient length to pass between the legs of the person using the apparatus 10. Where the person using the apparatus 10 is a manner, the length of the hose 14 should be sufficient to allow the discharge end to extend out of the fly portion of the person's pants, so that the contained liquid may be discharged in a manner that is physically similar to that in which a man might urinate into a cup.

In order to maintain the temperature of the liquid carried in the liquid container 12—for comfort or preservation reasons, for example—it may be desired to insulate the liquid container 12. As shown in FIGS. 1–4, one manner of accomplishing this is by position a layer of insulation material 20 along the base of the liquid container 12. The insulation material may be of foam or other suitable type. The positioning of the insulation material 20 along the base of the liquid container 12 is preferred, because it will not interfere with the insertion of the top portion of the liquid container 12 between the person's buttocks, and because the top and side portions of the liquid container 12 should be sufficiently warmed by the person's body.

In some instances, it may be desired to provide artificial heating means to preserve the liquid at a desired temperature. As shown in FIGS. 2–4, this may be accomplished by providing a space within the insulation material 20, into which may be inserted a heat packet 22 or other type of heating element. The space within the insulation material 20 should preferably extend therethrough, so that heat radiating from the heat packet 22 to directly contact the base of the liquid container 12.

Statement of Operation

To use the apparatus 10 of the present invention, a person will first fill the liquid container 12 with the desired fluid, such as urine. The person will then position the apparatus 10, with the upper portion of the liquid container 12 inserted between the person's buttocks, and the hose 14 extended between the person's legs. The cap 16 should be in the closed position on the discharge end of the hose 14.

When it is time to discharge the liquid, the person will remove or open the cap 16. If gravity is not sufficient to cause discharge of the liquid from the liquid container 12, the person may was to squeeze his or her buttocks tightly together to provide additional pressure on the liquid, helping to force it through the hose 14.

As discussed above, improved temperature maintenance of the liquid can be provided by providing an insulation material 20, and perhaps also a heat pack 22 in combination therewith.

While the invention has been particularly shown and described with reference to preferred embodiments thereof, it will be understood by those skilled in the art that the foregoing and other changes in form and details may be made therein without departing from the spirit and scope of the invention.

I claim:

1. An apparatus for transporting a liquid on the body of a person and discharging the liquid comprising, in combination:

a container adapted to contain a liquid;

wherein said container is dimensioned so that an upper portion thereof can be inserted between a person's buttocks;

a hose coupled at a first end thereof to said container; and one of a cap, valve, and plug inserted into a second end of said hose;

wherein said hose is of sufficient length to pass between said person's legs.

2. The apparatus of claim 1 wherein said container is wedge-shaped.

3. The apparatus of claim 1 wherein said container is comprised of a flexible material.

4. The apparatus of claim 3 wherein said flexible material is one of vinyl, plastic and rubber.

5. The apparatus of claim 1 further comprising insulation material attached to said container.

6. The apparatus of claim 2 further comprising insulation material attached to a base of said wedge-shaped container.

7. The apparatus of claim 1 further comprising a heating element attached to said container.

8. The apparatus of claim 6 further comprising a heating element attached to an underside of said insulation material and wherein said insulation material has an opening therein to permit heat radiating from said heating element to contact said base of said wedge-shaped container.

9. A method for transporting a liquid on the body of a person and discharging the liquid comprising:

providing a container adapted to contain a liquid;

placing said liquid in said container;

wherein said container is dimensioned so that an upper portion thereof can be inserted between a person's buttocks;

providing a hose coupled at a first end thereof to said container;

providing one of a cap, valve, and plug inserted into a second end of said hose;

wherein said hose is of sufficient length to pass between said person's legs;

inserting said upper portion of said container between said person's buttocks;

positioning said hose between said person's legs.

10. The method of claim 9 wherein said container is wedge-shaped.

11. The method of claim 9 wherein said container is comprised of a flexible material.

12. The method of claim 11 wherein said flexible material is one of vinyl, plastic and rubber.

13. The method of claim 9 further comprising attaching insulation material to said container.

14. The method of claim 10 further comprising attaching insulation material to a base of said wedge-shaped container.

15. The method of claim 9 further comprising attaching a heating element to said container.

16. The method of claim 14 further comprising attaching a heating element to an underside of said insulation material and wherein said insulation material has an opening therein to permit heat radiating from said heating element to contact said base of said wedge-shaped container.

17. The method of claim 9 further comprising the step of releasing said one of a cap, valve, and plug so as to permit said liquid to exit said second end of said hose.

* * * * *